United States Patent [19]

Montgomery

[11] 4,217,244
[45] Aug. 12, 1980

[54] REGENERATION OF ISOMERIZATION CATALYSTS CONTAINING MAGNESIUM OXIDE

[75] Inventor: Dean P. Montgomery, Bartlesville, Okla.

[73] Assignee: Phillips Petroleum Company, Bartlesville, Okla.

[21] Appl. No.: 905,074

[22] Filed: May 11, 1978

[51] Int. Cl.² .................... B01J 21/20; C07C 5/30
[52] U.S. Cl. ............................... 252/419; 252/420; 585/664
[58] Field of Search ............... 252/419, 420, 416, 418; 260/683.2; 585/664

[56] References Cited

U.S. PATENT DOCUMENTS

| | | | |
|---|---|---|---|
| 2,344,770 | 3/1944 | Gunness | 252/416 |
| 2,361,613 | 10/1944 | Drennan | 260/683.2 |
| 3,609,097 | 9/1971 | Koppe | 252/419 |
| 3,658,929 | 4/1972 | Banks | 260/683.2 |

*Primary Examiner*—P. E. Konopka

[57] ABSTRACT

A magnesium oxide-containing catalyst which has been used to isomerize butene-2 to butene-1 is regenerated at a localized bed temperature to not exceed about 1000° F., preferably not to exceed about 900° F., by steps involving purging the catalyst with an inert gas, then admixing with said gas oxygen or oxygen-containing gas to produce a final mixture to contain not more than about 0.5 volume percent $O_2$, and passing said mixture through the catalyst, controlling flow of the mixture to maintain the catalyst at a localized temperature not exceeding substantially about 1000° F., preferably not exceeding about 900° F., increasing the $O_2$ content of the mixture gradually, but not sufficiently to substantially exceed said temperature of about 1000° F., preferably 900° F., continuing to pass said mixture through the catalyst until substantially no more carbon oxides are detected in the gas exiting the catalyst, arresting flow of oxygen to the catalyst, continuing to pass said inert gas through the catalyst until substantially all $O_2$ has been purged therefrom, then purging said catalyst to prepare it for isomerization use.

3 Claims, 1 Drawing Figure

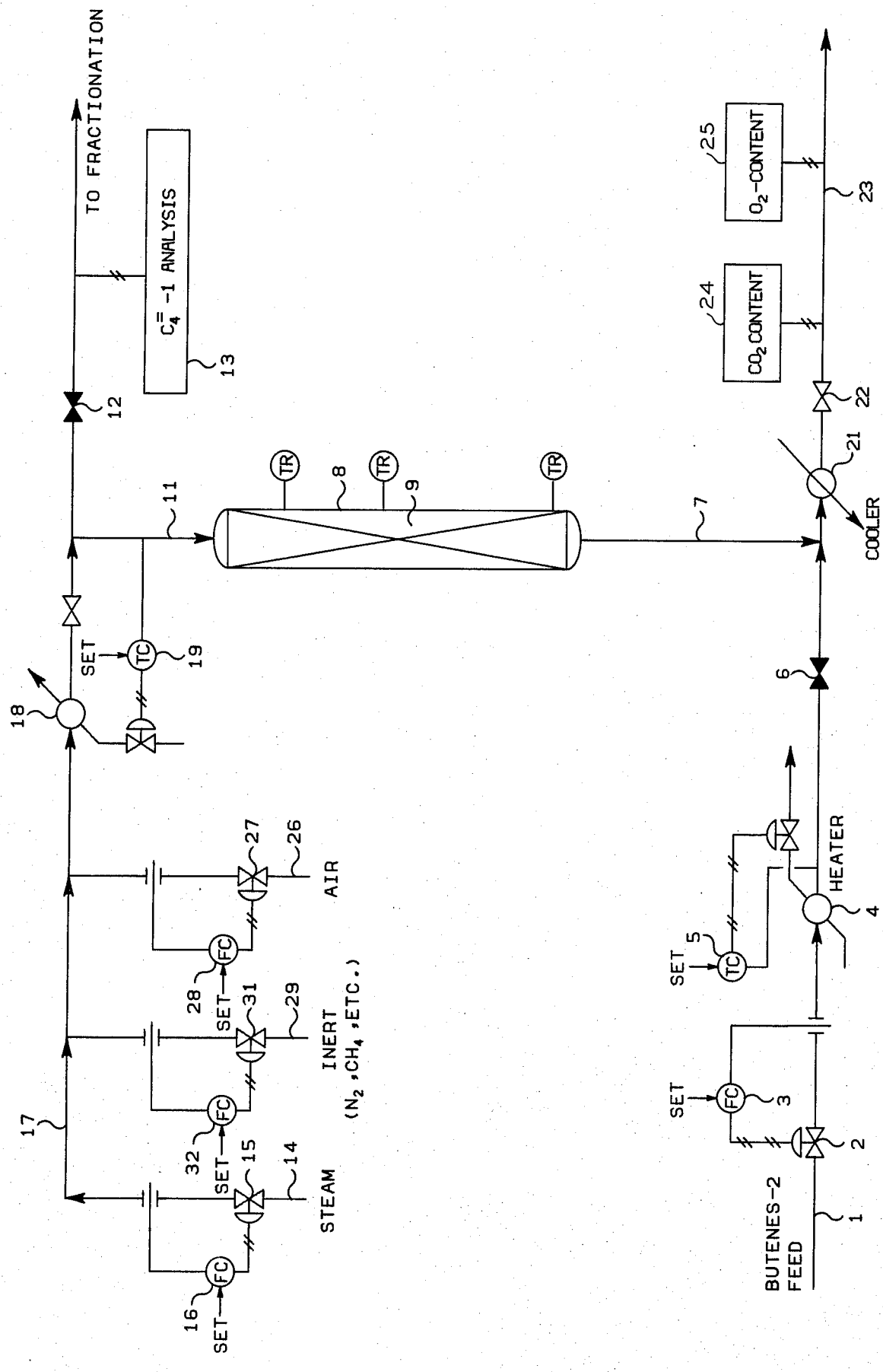

REGENERATION OF ISOMERIZATION CATALYSTS CONTAINING MAGNESIUM OXIDE

This invention relates to a method for the regeneration of a catalyst. In one of its aspects it relates to the regeneration of a magnesium oxide catalyst which has been employed for the isomerization of butene-2 to butene-1. In a more specific aspect of the invention it relates to a method of regenerating such a catalyst to provide maximum activity and effectiveness thereof upon regeneration to isomerize butene-2 to butene-1.

In one of its concepts the invention provides a series of steps involving purging hydrocarbon from the catalyst, then burning or combusting the carbonaceous material from said catalyst, under controlled conditions, then purging the catalyst of any residual oxygen, and then reusing the catalyst, the controlled conditions including not exceeding a temperature of about 1000° F., preferably about 900° F., during the combustion of the carbonaceous material from the catalyst and an initial oxygen content during initial combustion of the catalyst of not more than about 0.5 volume percent $O_2$ and the gradual increase of $O_2$ content of the combustion effecting gas mixture, but always insufficiently so as to not exceed a temperature substantially above about 1000° F., preferably about 900° F.

The regeneration or reactivation of various catalysts used for various conversions including cracking, reforming, desulfurization and the like, are known in the art of hydrocarbon conversion. Thus, in U.S. Pat. No. 2,353,508 issued July 11, 1944, Walter A. Schulze, the disclosure of which is incorporated herein by reference, there is set forth a process for reactivation of a catalyst or solid contact catalyst mass which has been more or less progressively inactivated by deposition of carbon and/or carbonaceous material on the catalyst particles by initiating combustion by reaching ignition with presence of oxygen and thereafter controlling the combustion by limiting the amount of oxygen reaching the combustion zone, thus to prevent excessive combustion temperatures. On page 2, in column 1, a three-step process is set forth which involves purging with steam, initiating combustion and then when ignition has been effected, cutting off steam and air, cycling effluent gas through a cooler while introducing air to the recycle effluent and regulating the added air to control the combustion temperature. Although the patent does not state the initial amount of oxygen it does state, in describing step 2, that the oxygen will be not over about 10 percent by volume, but will be sufficient to cause an ignition, and this at a temperature between about 800° and about a 1000° F. The patent further states that generally, a temperature of 900° F. is employed. It will be noted that the patent also states that as soon as combustion begins, the temperature of the effluent sharply rises above that of the infeed to a level of at least 1000° F. and frequently higher, say to 1200° or to 1300° F. Still further, the patent states that the combustion temperature in the catalyst is kept within proper limits, namely substantially above 900° F. but not above about 1400° F. The patent further states that in general the temperature of the infeed will be at between about 800° and about 900° F. and its oxygen content between about 2 percent and about 10 percent. Finally, the patent states that conditions are maintained until the temperature of the effluent gas drops to a predetermined level substantially below the maximum attained, usually to about 1100° F. indicating that the major part of the combustible material has been burned off and that the exothermic heat of regeneration is much less.

U.S. Pat. No. 3,962,126 issued June 8, 1976 discloses a method of reactivating a carbonized magnesium oxide catalyst which has been used in a phenol alkylation reaction by burning carbon therefrom and then contacting a partially reactivated catalyst thus obtained with water at a temperature below 300° C. to restore its activity.

U.S. Pat. No. 2,417,359 issued Mar. 11, 1947, Jesse A. Guyer discloses removal of carbon during catalyst reactivation and monitoring oxygen in the gas effluent of the catalyst.

I have now discovered that high efficiency and activity of a magnesium oxide-containing catalyst used in the plant for the isomerization of butene-2 to butene-1, can be obtained provided the localized catalyst bed temperature is controlled at all times to not exceed about 1000° F., preferably to not exceed about 900° F. during the entire regeneration or reactivation operation.

It is an object of this invention to provide a method for the regeneration of a catalyst. It is another object of this invention to provide a method for the regeneration of a magnesium oxide-containing catalyst to remove carbonaceous material therefrom. It is a further object of this invention to provide a method for the regeneration of a catalyst which is used in the isomerization of a hydrocarbon. It is a still further object of this invention to provide for the reactivation of a magnesium oxide-containing catalyst which has been used, and will be used again, for the isomerization of butene-2 to butene-1.

Other aspects, concepts, objects and the several advantages of this invention are apparent from a study of this disclosure, the drawing and the appended claims.

According to the present invention there is provided a method for regenerating a used catalyst consisting essentially of magnesium oxide and which has been used to isomerize butene-2 to butene-1 which comprises 1. Purging the used catalyst which, after it has been used for isomerization, is at a temperature of about 800° F., with an inert gas at a temperature of the order of about 800° F. to remove substantially any hydrocarbon remaining in the catalyst bed, 2. Then passing an oxygen-containing gas together with said inert gas, the mixture to contain not more than about 0.5 volume percent $O_2$, through the catalyst, 3. Controlling the rate of flow of said mixture to maintain the catalyst at a localized bed temperature not exceeding substantially about 1000° F., 4. Now increasing the $O_2$ content of the mixture gradually, but not sufficiently to substantially exceed said localized bed temperature of about a 1000° F., 5. Continuing to pass $O_2$-containing gas to the catalyst until substantially no more carbon oxides exit the catalyst bed in the off-gas indicating the carbonaceous material has been substantially completely burned off from the catalyst, 6. Then stopping the flow of $O_2$ to the catalyst, and 7. Continuing to pass said inert gas through said catalyst bed until substantially all $O_2$ has been purged from said catalyst bed.

Also according to the invention, when the inert gas used is steam, it will be purged from the catalyst with a gas such as methane, prior to using the catalyst for further isomerization. In any event, the temperature of the catalyst is adjusted to about 800° F. before the catalyst is again used to isomerize butene-2.

Preferably, according to the invention, the temperature at no time will exceed substantially about 900° F. for best results, as indicated by data herein.

Presently, the preferred inert gas is steam and the gas preferred is methane for purging the catalyst prior to reuse. These materials are available, ordinarily, in the refinery.

Also, the temperature of the methane will be such as to adjust, in a reasonable time, the temperature of the catalyst bed to the desired amount, 800° F.

Referring now to the drawing, a butenes-2 feed is passed by 1 through flow control valve 2 controlled by flow control 3 through a heater 4 on temperature controller 5 and valve 6 by 7 up through catalyst bed 9 in reactor 8 and from catalyst bed 9 up through 11 and valve 12 in 17 to fractionation not shown. Analysis of the effluent gases is accomplished at 13.

During this operation, as just described, the catalyst which is a magnesium oxide catalyst effective to substantially isomerize the butene-2 to butene-1, will accumulate carbonaceous deposit.

Still, referring to the drawing, a catalyst bed and the flow thereto and therefrom, just described, is arrested by blocking off valves 6 and 12. Regeneration is then commenced.

Valve 22 is opened. Steam is passed by 14 through valve 15 on flow control 16 through 17 and heater 18 on temperature control 19 by 11 into the catalyst bed 9. Residual hydrocarbon in the bed is removed at 7 and from the system by way of cooler 21, valve 22 and 23.

When substantially all hydrocarbon has been purged from the bed 9, air is passed by 26 through valve 27 on flow control 28 through heater 18 and 11 into the catalyst bed. The mixture of the air and steam is controlled to contain no more than about 0.5 $O_2$ and the mixture is passed at a rate to maintain the localized temperature of the bed of catalyst not above about 1000° F., preferably not above 900° F. Combustion gas containing effluent 7 is passed by cooler 21 and valve 22 through 23 from the operation. The effluent is monitored at 24 for its carbon oxides content. This is continued until substantially all carbonaceous material has been removed from the catalyst. The flow of air is discontinued, but the flow of steam is continued until the oxygen content, monitored at 25, indicates that there is no further appreciable oxygen in the catalyst bed. Then, an inert gas such as nitrogen, but presently methane is preferred because of its ready availability, is passed by 29 through valve 31 on flow control 32 into 17, through heater 18 and 11 into bed 9, to prepare the bed for isomerization by removing any undesired traces of steam or water therefrom.

In passing, it is noted, that the butene-2 feed should be pretreated to remove moisture therefrom. It is now preferred to pretreat the butene feed with a dehydrating or desiccating agent. Such desiccating agents are well known. A 13×molecular sieve made by Linde has been found highly effective to prepare the butene-2 suitably for the insuing isomerization to butene-1.

When nitrogen is used as the inert gas, no separate purging of the catalyst to remove water therefrom may be needed.

TABLE I (See explanation below table.)

| Run No. | Average of Mol % Butene-1 in Product Butenes for | | | Max. Mol % Butene-1 in 24 Hr. Period | Relative Activity % | Calculated Wt. % Coke on Catalyst at End of Run |
|---|---|---|---|---|---|---|
| | 6 Hrs. | 12 Hrs. | 24 Hrs. | | | |
| 1 | 22.9 | 23.1 | 23.5 | 24.0 | 100 | 0.22 |
| 2 | 7.6 | 10.0 | 13.1 | 19.6 (37 Hrs.) | 56 | 0.11 |
| 3 | 14.2 | 15.9 | 17.7 | 20.2 | 75 | — |
| 4 | 15.4 | 15.7 | 16.0 | 16.3 | 68 | 0.20 |
| 5 | 15.3 | 16.3 | 17.2 | 18.3 | 73 | 0.21 |
| 6 | 16.2 | 17.8 | 17.6 | 19.0 | 75 | 0.32 |
| 7 | 23.6 | 23.9 | 24.0 (18 Hrs.) | 24.3 | 100 | 0.20 |
| 8 | 21.5 | 21.7 (10 Hrs.) | — | 22.1 | ~90 | 0.24 |
| 9 | 22.2 | 22.1 | 22.1 (15 Hrs.) | 22.6 | ~92 | 0.63 |
| 10 | 20.2 | 20.4 (10 Hrs.) | — | 20.6 | ~85 | — |
| 11 | 23.5 | 23.8 | 24.6 | 25.5 | 100 | 0.30 |
| 12 | 22.0 | 22.5 | 23.1 | 24.3 | 95 at 18 Hrs. | 0.26 |
| 13 | 21.4 | 22.8 | 23.8 | 24.9 | 97 | — |
| 14 | 21.2 | 22.3 | — | 24.0 | 94 at 11 Hrs. | — |
| 15 | 24.5 | 24.2 | — | 24.8 | 102 at 11 Hrs. | — |
| 16 | 22.8 | 21.8 | 21.1 (15 Hrs.) | 23.5 | 88 at 15 Hrs. | — |
| 17 | 19.0 | 15.4 | 14.6 | 20.7 | 59 | 1.45 |
| 18 | 15.5 | 13.9 (10 Hrs.) | — | 18.1 | 59 at 10 Hrs. | 0.27 |
| 19 | 18.3 | 16.8 | — | 19.9 | 100 | 0.81 |
| 20 | 19.3 | 20.3 | 22.6 | 25.1 | 119 at 10 Hrs. (90% compared to Run 11) | 0.11 |
| 21 | 21.3 | 22.7 | 23.8 | 24.9 | 133 at 10 Hrs. (97% compared with Run 11) | 0.27 |
| 22 | 23.6 | 24.0 | 24.1 (17 Hrs.) | 24.4 (17 Hrs.) | 143 at 10 Hrs. (99% at 17 Hrs. compared to Run 11) | — |
| 23 | 23.3 | 22.7 | 23.8 | 24.1 | 141 at 10 Hrs. | — |

TABLE I-continued (See explanation below table.)

| Run No. | Average of Mol % Butene-1 in Product Butenes for | | | Max. Mol % Butene-1 in 24 Hr. Period | Relative Activity % | Calculated Wt. % Coke on Catalyst at End of Run |
|---|---|---|---|---|---|---|
| | 6 Hrs. | 12 Hrs. | 24 Hrs. | | | |
| | | (19 Hrs.) | | (19 Hrs.) | (98% at 19 Hrs. compared with Run 11) | |

A. Discussion of Data Runs 1–23

Catalyst used to effect conversion of (double bond isomerizing of) butenes-2 to butene-1 was magnesium oxide containing about 5 weight percent $SiO_2$.

When butenes-2 are double bond isomerized to butene-1 using this catalyst, after about one day's operation, the activity of the catalyst was depleted by accumulated deposits. The catalyst activity was restored by burning off the accumulated deposits. However, the procedure for optimum removal of the deposits and restoring the activity of the catalyst to convert butenes-2 to butene-1 was relatively critical so that catalyst damage did not occur, as determined from the following:

Runs 1–6

Fresh catalyst as received, was used in Run 1 and was assigned an activity of 100 percent. The equilibrium ratio (volume) of butene-1 to butene-1 plus butenes-2 at 800° F. is 0.26, or 26 volume percent butene-1 in the total n-butenes.

The new catalyst, in Run 1, was used to isomerize pure butenes-2 to butene-1. In all runs butenes-2 were charged at 800° F., 120 psig., 5 WHSV (weight hourly space velocity of 5 pounds of feed per pound of catalyst per hour), 1600 VHSV or GHSV (vlume of vaporous or gaseous feed per hour per volume of catalyst was 1600). The average volume percent butene-1 in the product total butenes in 24 hours operation was 23.5. This value is used as 100 percent basis using the new catalyst in Run 1.

The spent catalyst from Run 1 was regenerated "conventionally". The catalyst was heated to 1000° F. using flowing nitrogen and then a regeneration gas was charged until no $CO_2$ appeared in the off-gas. Pressure for regeneration was one atmosphere. The regeneration gas volume percent composition was: air 10, steam 45, and nitrogen 45. The VHSV or GHSV was 1,300 during regeneration. This catalyst from Run 1 was not dried 6 hours with nitrogen at 1000° F. before it was used in Run 2.

Run 2 was operated at the same reaction conditions set out above for Run 1. The average volume percent butene-1 in the product butenes in 24 hours operation was only 13.1. This 13.1 compared with 23.5 of Run 1 is but 56 percent relative activity, Run 1 was set as being 100 percent activity.

The spent catalyst from Run 2 was regenerated as was used (above) for Run 1's regeneration except that the catalyst was post dried at 800° F. with nitrogen for 19.5 hours.

Run 3 used this thusly regenerated catalyst from Run 2 and the average volume percent butene-1 in the product butenes in 24 hours was 17.7. This 17.7 compared with the base Run 1 value of 23.5 resulted in 75 percent relative activity.

The used catalyst from Run 3 was regenerated in the same manner used for the used catalyst from Run 1 except the catalyst was post dried for 6 hours with nitrogen at 1000° F.

Run 4 used the catalyst regenerated at Run 3 under the same isomerization conditions as set out for Run 1. The average volume percent butene-1 in the product total butenes in 24 hours was 16.0 or 16.0/23.5 giving a relative activity of only 68. In this Run 4 the 1000° F. post treatment decreased the activity of the regenerated catalyst.

The catalyst from Run 4 was regenerated as in Run 1, but there was no steam in the regeneration gas and no post drying period.

Run 5 used the regenerated catalyst from Run 4, operated for isomerization as in Run 1, and the average volume percent butene-1 in the product total butenes in 24 hours was 17.2 or 17.2/23.5, which resulted in a relative activity of 73.

The used catalyst from Run 5 was regenerated in the same manner as the used catalyst from Run 4 (a repeat run).

Run 6 used this regenerated catalyst from Run 5. The average volume percent butene-1 in the product butenes in 24 hours was 17.6 or 17.6/23.5 and resulted in a relative activity of 75.

Runs 7–10

Run 7 used new catalyst as received. The conversion to butene-1 percent, as used hereinbefore, was 24.0. This was set at 100 percent activity.

The used catalyst from Run 8 was regenerated as in Run 1, but there was no steam in the regeneration gases and no post drying was used. The butene-1 value was between 21.7 at 10 hours and 22.1 (maximum). The relative activity was about 90 percent.

Runs 9 and 10 used the same regeneration steps as used for Run 7's used catalyst. The butene-1 values were, respectively, about 22.6 and about 20.6. The relative activities were about 90 percent of the base Run 7.

Runs 11–18

Plant butene-2 feed was used in these runs, the isomerization reaction conditions being the same as above in Runs 1 through 10. The feed was pretreated over molecular sieve, type 13X.

Run 11 again used new catalyst. The conversion to butene-1 was 24.6, and this was set at 100 percent activity.

Used catalyst from Run 11 was regenerated with steam containing air, the air being added gradually to increase the oxygen volume percent from about 0.5 to about 1.5 to 2 percent. The catalyst was then dried at 800° F. with nitrogen.

Run 12 used the regenerated catalyst from Run 11 and the butene-1 value was 23.1. This resulted in a relative activity of about 94 percent.

The used catalyst from Run 12 was regenerated in the same way as the used catalyst from 1 was regenerated.

Run 13 used the regenerated catalyst from Run 12 and the butene-1 value was 23.8. This resulted in a relative activity of about 97 percent.

The used catalyst from Run 13 was regenerated at 800° F. using a gas of 90 volume percent nitrogen and 10 volume percent carbon dioxide saturated with water at 75° F. and "spiked" gradually with air to increase oxygen from about 0.5 to about 2 percent by volume.

This regenerated catalyst from Run 13 was used in Run 14. The butene-1 value was, at the 11 hour value, 22.3, or the relative activity was about 91 percent. Based on Run 11 at 24 hour average this value was about 94 percent based on Run 11 at its 11 hour value of 23.8 butene-1.

Runs 15, 16, and 17 catalysts were regenerated in the way used for the catalyst used in Run 14. The butene-1 values and relative activities were, respectively: 24.2 (11 hours) and 102 percent; 21.1 (15 hour value) and 88 percent; and 14.6 and 59 percent. These Runs 16 and 17 cannot be explained as to the cause of low relative activities, but were probably caused by spent molecular sieve used for feed pretreatment.

Run 18 also cannot be explained at the low relative activity.

Runs 19–23

New catalyst was charged and plant butene-2 was again used, the isomerization reaction conditions were used as set out hereinbefore.

Run 19 (base run) produced a low butene-1 value of 19.9 maximum. This value was 16.8 at 10 hours. This was the new base run.

The molecular sieve bed was switched to a freshly regenerated bed for feed pretreatment.

Run 20 used catalyst from Run 19 which was regenerated at 800° F. using steam "spiked" with air to gradually increase the oxygen from about 0.5 to about 1.5 to 2 volume percent in the regeneration gas. The catalyst was then dried at 800° F. with nitrogen.

Run 20 resulted in butene-1 of 22.6 at 24 hours, but 20.3 at a comparable 10 hours (compared with 16.8 at 10 hours of Run 19, the relative activity was about 119). Compared with Run 11 at 24 hours, the relative activity was about 90 percent.

Run 21 used the catalyst from Run 20 after regeneration as was done for catalyst for Run 20. The butene-1 value was 23.8 at 24 hours and compared with Run 11 was about 97 percent activity. (Compared with Run 19 at 10 hours, the relative activity was about 133 percent.)

The catalyst from Run 21 was regenerated at 800° F. using an inert gas of 90 volumes of nitrogen and 10 volumes of $CO_2$, saturated with water at 75° F. and "spiked" with air gradually to increase oxygen from 0.5 to 2 volume percent.

Run 22 compared with Run 11 gave a relative activity at 17 hours of 99 percent. (Compared with Run 19 at 10 hours, the relative activity was 143 percent.)

Run 23 used the catalyst from Run 22 regenerated as the catalyst which was used for Run 22. The relative activity of Run 23 as compared with Run 11 was about 98 percent. (Compared with Run 19 at 10 hours, it was 141 percent.)

B. Conclusions

The improved regeneration followed Run 11, using fresh catalyst as 100 percent activity or base run.

The inventions regeneration procedure, based on the data herein, is as follows (see Runs 11–13):

Pressure—1 atmosphere;
Temperature—800° F.

Procedure Established

Hour 1:

The depressured reactor is stripped for one hour with steam at 7 SCFH on a catalyst volume of 280 cubic centimeters.

Hour 2:

To the steam flow above, add about 0.2 SCFH air to achieve about 0.5 volume percent $O_2$ in the total gas or vapor.

Hour 3:

Increase the air to about 0.4 SCFH so that $O_2$ content is about 1 volume percent.

Hour 4:

Increase the air to about 0.8 SCFH to effect about 2 volume percent $O_2$ in the gas.

Hour 5 Plus:

Continue regeneration at 800° F. and one atmosphere with steam containing the about 2 volume percent oxygen until no more carbon oxides are found in the off-gas from regeneration (no more coke is being burned off).

At no more carbon oxides in the off gas, the air is stopped but the steam is continued for one more hour until no $O_2$ appears in the off gas. The relative activity of the catalyst will be 95 to 97 percent of the new catalyst.

Optionally, 800° F. $N_2$ purge or methane purge at 800° F. can be used for 0.5 to 1 hour to remove the $H_2O$ from the regenerated catalyst.

The catalyst is now regenerated, and is at 800° F. or the isomerization reaction temperature and isomerization of butenes-2 to butenes-1 is now commenced.

The following information is given by way of further description of the details of the invention.

New catalyst is assigned a relative activity of 100 percent, and in tests described herein this means the isomerized effluent contained 26 volume percent butene-1.

Normally when the relative activity falls to about 85 percent (about 22 volume percent butene-1 in the effluent), regeneration of the catalyst is effected.

A plant can run, e.g., 24 hours on the isomerization cycle (before too low conversion of butenes-2 to butene-1 occurs) and about 6 to 12 hours on the regeneration cycle of this invention, described in detail hereinbelow.

During isomerization of butenes-2 to butene-1 over MgO fixed bed catalyst (about 95 weight percent MgO, 5 weight percent $SiO_2$) the reaction is effected at about 800° F., 120 psig, and 5 weight hourly space velocity (WHSV), which means 5 pounds of butenes-2-containing feed per pound of catalyst per hour, which is equivalent to about 1600 volumes of vapor feed per pound of catalyst per hour, referred to as VHSV-vapor hourly space velocity or as GHSV-gas hourly space velocity in butenes-2 isomerization.

When the isomerization cycle is completed and regeneration of the catalyst is required, the feed flow is stopped and the reactor is depressured, to suitable facilities, down to about one atmosphere pressure. The reactor is still at about 800° F., the preselected reaction temperature.

The regeneration cycle commences with first adding steam, at this 800° F., for a time sufficient to remove from the system hydrocarbons (butenes-2 and butene-1) so that a regeneration gas, free oxygen-containing gas, e.g., air, can be charged safely to the system to combust the carbonaceous deposit at a rate not to exceed about 1000° F. (extreme maximum), preferably not to exceed 950° F., and more preferably not to exceed 900° F. at any locality in the catalyst bed.

While steam is still flowing into the catalyst bed, the free-oxygen gas, e.g., air, at about this 800° F., is added at a rate to prevent the bed of catalyst from being heated at any locality (due to exothermic combustion of the carbonaceous deposits) to above a preset maximum temperature, e.g., 900° F. After a period of time, or gradually, the amount of free oxygen-containing gas, e.g., air, added is increased, but still at an amount or rate to not overheat the catalyst bed. When the carbon oxides-content of the regeneration off-gas is at the desired low level, e.g., even zero, the air flow is stopped, with steam still flowing until the air is purged from the system, as indicated by the $O_2$-content of the regeneration off-gas being zero. After the $O_2$-content is zero, steam flow can be continued for a period of time, and then the steam flow can be stopped, and the steam purged out by means of 800° F. inert gas such as nitrogen, or usually such as methane in a plant operation.

800° F. has been used above since this is the now-optimum temperature selected for the isomerization reaction. The temperature of the added gases during regeneration are usually at the preselected isomerization operation temperature, and in the specific operation herein described is 800° F.

After the purging of the steam from the catalyst system is complete, using methane or nitrogen, and the bed of catalyst is at 800° F., butenes-2 feed is started, thus beginning another isomerization cycle.

Typical Run Based on Pilot Plant Run and Plant Flow Scheme

As described, during the isomerization cycle, vaporous butenes-2 feed flows via conduit 1 and valve 2 on flow control 3, preheated to 800° F. (120 psig, 5 WHSV) in (4) on temperature control 5, via valve 6, conduit 7 into reactor 8 containing fixed bed double bond isomerization catalyst 9 (95 weight percent MgO, 5 weight percent $SiO_2$). Butenes-2 are, in part, isomerized to butene-1. Reactor effluent 11 is passed via valve 12 to fractionation (not shown).

When the butene-1 content of the butene-1-butenes-2 effluent in 11 falls to below a preselected volume percent, e.g., 22 volume percent in this example, based on pilot plant run data, the flow of feed 1 is stopped by allowing valve 2 to be closed. An analyzer 13 or laboratory analysis can be used to determine butene-1 content of the reactor effluent. Optionally, valve 6 can be closed. The reactor 9 is depressed via line 11 and valve 12 to about one atmosphere absolute pressure. Then, valve 12 is closed.

The regeneration cycle is started.

In a specific run made on pilot plant operations, the following procedure successfully reactivated the "spent" isomerization catalyst to about 95 to 97 percent of original activity.

Step 1: for a first hour, 800° F. steam (reactor temperature is 800° F.) was charged by line 14 at a gas space velocity of 1300 standard cubic feet of steam per cubic foot of catalyst per hour. The steam passed via 14, valve 15, on flow control 16, line 17, optional heat exchanger 18 on temperature control 19, to effect the 800° F. temperature of the steam, conduit 11, through reactor 8 containing the "spent catalyst" 9, conduit 7, cooler-condenser 21, and open valve 22. The mass passed to a liquid-vapor separator (not shown) to remove condensed steam, and the gas was vented via 23.

This steam flow purged the hydrocarbon materials from the system so that an oxygen (free oxygen)-containing gas could be charged, e.g., air, in this run.

Step 2: with steam flowing as in step 1, for the next hour, or hour two, air was charged at 800° F. along with the steam in an amount whereby the free oxygen content of the total mass was 0.5 volume percent oxygen. This air was passed via line 26, valve 27 on flow control 28, exchanger 18, line 11, reactor 8, through catalyst 8, line 7, cooler-condenser 21, valve 22 (to liquid-vapor separator, not shown), and the off-gas removed at 23. This original low $O_2$-content steam is at a level so that the catalyst bed 9 temperature will not exceed about 900° F. The localized temperature increase was from about 800° F. to about 890° F.

Step 3: after about one hour of gentle combustion, as in Step 2, additional air was added, as described in Step 2, above, with the free oxygen content of the total regeneration gas flow being at about one volume percent. This flow was continued for one more hour, or hour three. The localized bed 9 temperature did not exceed 900° F.

Step 4: after about one hour, as in Step 3, there was added additional air until the free oxygen content of the mass in 11 was about two volume percent oxygen (free oxygen). This regeneration fluid (two percent free oxygen in steam) was continued for one more hour, hour four. The localized catalyst bed temperature did not exceed 900° F.

Step 5: the flow of stream 11, as set out in Step 4, was continued until analyzer 24 indicated there were no more carbon oxides in the off-gas in 23. When the carbon oxides content was zero, the air flow via 26 was stopped (valve 27 was closed).

Step 6: steam flow, as described in Step 1, was continued for about one more hour until the free oxygen content of gas 23, as measured by oxygen analyzer 25 (or laboratory analysis) showed zero oxygen. (At zero oxygen, hydrocarbon can be added to the reactor).

Step 7: steam flow via 14 was stopped (valve 15 was closed) and, in the pilot runs, nitrogen was used as the inert gas to sweep out the steam before the catalyst was placed back on the isomerization cycle. In a plant usually methane is this inert gas. To flow in nitrogen (or methane), the inert gas enters at 800° F. via line 29, valve 31 on flow control 32, heater 18, line 11, reactor 8 and catalyst 9, line 7, cooler-condenser 21, valve 22 (and liquid-vapor separator, not shown). The inert gas is removed to downstream facilities (not shown) via 23. This purge to remove steam usually is about one-half to about one hour duration.

The catalyst has now been reactivated and is ready to receive the feed hydrocarbon on the isomerization cycle.

The essence of this catalyst reactivation method is the regeneration of the catalyst in which the localized bed temperature does not exceed about 900° F. (1000° F. maximum, preferably not above 950° F., and preferably about 900° F. maximum), and this is accomplished by using steam containing that amount of added free-oxygen to attain this temperature. The example used stagewise increase in free $O_2$ in steam (0.5 volume percent initially when maximum coke at outset of regeneration was on the catalyst and then up to 2 volume percent free oxygen when the coke has been substantially removed from the catalyst). This free $O_2$-content increase could, by gradual increase, be added in an amount so that the bed 9 temperature will not exceed the preferred 900° F. maximum.

Reasonable variation and modification are possible within the scope of the foregoing disclosure, the drawing and the appended claims to the invention the essence of which is that a magnesium oxide isomerization catalyst suited for the isomerization of butene-2 to butene-1 can be regenerated to provide high activity of the catalyst for said isomerization by controlling the entire regeneration operation to maintain the temperature of the catalyst at a temperature not substantially above 1000° F. and preferably at a temperature not substantially above a temperature of the order of about 900° F.

I claim:

1. A method for regenerating a used catalyst consisting essentially of magnesium oxide, which has been used to isomerize butene-2 to butene-1, which comprises purging the used catalyst with an inert gas at a temperature substantially below about 1000° F., to remove substantially any hydrocarbon remaining in the catalyst, then passing an oxygen-containing gas, together with said inert gas, the mixture to contain not more than about 0.5 volume percent $O_2$, through the catalyst, controlling the rate of flow of said mixture to maintain the catalyst at a localized bed temperature not exceeding substantially about 1000° F., now increasing the $O_2$ content of the mixture gradually but not sufficiently to substantially exceed said temperature of about 1000° F., continuing to pass $O_2$-containing gas through the catalyst until substantially no more carbon dioxide exits the catalyst bed in the off-gas therefrom, then stopping the flow of $O_2$ to the catalyst, continuing to pass said inert gas through said catalyst bed until substantially all $O_2$ has been purged from said catalyst bed and then removing any traces of water or steam from said catalyst prior to its reuse and then reusing said catalyst.

2. A method according to claim 1 wherein the temperature is maintained at a level not exceeding one of the order of about 900° F. localized bed and the inert gas is steam.

3. A method according to claim 1 wherein the water or steam is purged from the catalyst using methane at a temperature of the order of about 800° F.

* * * * *